United States Patent [19]

Tong

[11] Patent Number: 4,479,958

[45] Date of Patent: Oct. 30, 1984

[54] METHODS AND COMPOSITIONS FOR INHIBITING HERPES VIRUS USING PYRIDINYL KETONES

[75] Inventor: Yulan C. Tong, Walnut Creek, Calif.

[73] Assignee: The Dow Chemical Company, Midland, Mich.

[21] Appl. No.: 942,100

[22] Filed: Sep. 13, 1978

[51] Int. Cl.³ .......................................... A61K 31/455
[52] U.S. Cl. .................................................. 424/266
[58] Field of Search ........................................ 424/266

[56] References Cited

PUBLICATIONS

Denton et al., J. Amer. Chem. Soc., 71, pp. 2048–2050, (1959).

Primary Examiner—Jerome D. Goldberg
Attorney, Agent, or Firm—Stephen L. Nesbitt; Gary D. Street; Raymond A. McDonald

[57] ABSTRACT

Methods and compositions for inhibiting herpes virus on living or non-living substrates by use of various pyridinyl ketones or a pharmaceutically-acceptable salt thereof.

5 Claims, No Drawings

METHODS AND COMPOSITIONS FOR INHIBITING HERPES VIRUS USING PYRIDINYL KETONES

BACKGROUND OF THE INVENTION

Herpes infections in mammals are caused by large lipid enveloped DNA viruses referred to as herpes viruses. Examples of mammalian diseases caused by herpes viruses include herpes simplex infections, chicken pox, shingles, cytomegalovirex infections, bovine mastitis, pseudorabies infections of pigs and cattle, and rhinotracheitis infections. A common response in herpes infections is the formation of a vesicular eruption of the skin, mucocutaneous tissue, eye, or mucus membranes. Clinical manifestions of herpes infections have been demonstrated in a number of species of mammals including man, monkeys, mice, rats, guinea pigs, cats, cattle, pigs and rabbits.

Herpes infections are commonly self limiting but are frequently recurring. Infections can become systemic and lead to death or severe disability. Herpes infections frequently involve the urogential area, the affected organs being the cervix, vulva, vagina, and urethra in females and the penis and urethra in males. It has been involved in localized and generalized infections of newborns, the infection usually being transmitted during delivery on passage through the infected birth canal.

SUMMARY OF THE INVENTION

The present invention is directed to a method for inhibiting herpes virus which comprises contacting the herpes virus and a substrate infected therewith with an effective virus inhibiting amount of a pyridinyl ketone of the formula

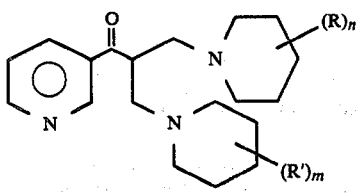

wherein R and R' independently represent a lower alkyl having from 1 to about 3 carbon atoms; n and m independently represent the integer 0 or 1.

The present invention is further directed to novel alkyl-substituted compounds falling within the generic formula wherein at least one alkyl group must be present on one or both of the piperidinyl moieties.

The present invention includes the "pharmaceutically-acceptable salts" of the pyridinyl ketones, that is the salts of the active compounds the anions of which are relatively non-toxic and innocuous to mammals at dosages or concentrations consistent with good antiviral activity so that the side effects ascribable to the anions do not vitiate the beneficial effects of the pyridinyl ketones. Suitable pharmaceutically-acceptable salts which can be employed in the method and composition of the invention include those derived from mineral acids such as the hydrochloride, hydrobromide, phosphate, nitrate and sulfate salts, those derived from organic carboxylic acids such as succinate, tartrate, citrate, malate, maleate, and acetate salts and those derived from organic sulfonic acids such as the methanesulfonate and toluenesulfonate salts.

The present invention also includes compositions useful for inhibiting herpes virus comprising an effective virus inhibiting amount of the pyridinyl ketone or a pharmaceutically-acceptable salt thereof in combination with a suitable pharmaceutically-acceptable non-aqueous carrier.

The compounds, method and compositions described herein may be used to inactivate the virus in vitro, i.e. in the absence of living tissue (as for example by contacting a non-living substrate contaminated with herpes virus), or in vivo by administering an effective virus inhibiting amount of the pyridinyl ketone to a mammal infected with herpes in a manner effective to result in contact and exposure of the virus to the compound.

DETAILED DESCRIPTION OF THE INVENTION

One method for preparing the pyridinyl ketones used in carrying out the present invention is by means of the Mannich reaction. In this procedure 3-acetyl-pyridine is reacted with formaldehyde and piperidine or a preselected piperidine having a lower alkyl substitution on the ring. See. *J. Amer. Chem. Soc.* 71, 2048 (1959).

In practicing the method of the invention a herpes virus is contacted with one or more of the pyridinyl ketones described herein in an amount sufficient to inactivate the virus. In vitro operations can be used to inactivate viruses in contaminated liquids, such as solutions or suspensions, or on solid substrates and surfaces such as bedding, garments, dental equipment, vaginal speculae, forceps, examination tables, gloves, milking machines, and the like which may become contaminated with infective herpes viruses. In addition, the active compounds can be incorporated in air filters, screens or the like to inactivate air born viruses passed therethrough.

The contacting of the herpes virus with the pyridinyl ketone can also be carried out in vivo by administering an effective virus inhibiting amount of the active compound to a mammal infected with herpes virus in a manner calculated to result in contact and exposure of the virus to the compound. The pyridinyl ketone compounds described herein are most desirably applied topically to the infected mammal, but other means of contacting the virus with an effective virus inhibiting amount of the active compound, which are known to those skilled in the art, may be indicated by the particular circumstances. In the case of topical application an effective virus inhibiting amount of the compound is applied topically to the infected site. The infected site is defined as an area infected by herpes virus which is characterized by swelling, erythema, vesicular lesion or eruption, the signs of which are in some cases preceded by prodomal symptoms such as for example a sensation of tingling, heat or pain at the infected site.

As used in the specification and claims the term "substrate" refers to any material living or non-living which is infected or may become infected with herpes virus. The term therefore not only includes non-living substrates already given above but living tissue, cells, body fluids and such.

The amount of the pyridinyl ketone to be employed can be referred to as an "effective virus inhibiting amount" or "antiviral amount", it being understood that sufficient compound is employed to achieve significant viral inhibition. The antiviral amount of the compound, that is the amount of the pyridinyl ketone compound sufficient to provide the desired effect, depends on various known factors such as type of contacting, in vitro or in vivo operations, concentration of the active compound, exposure time (contact time), type of virus involved, degree of viral contamination or infection, the size, type, age and condition of the animal to be treated, locus of infection in the animal, the particular compound or pharmaceutically-acceptable salt employed, the method of administration, and the degree of inhibition desired.

In the case of topical application an effective virus inhibiting amount is that amount required to cover the infected site and/or the immediately surrounding area (to prevent spread of the infection) with an antiherpetic concentration of the active compound in a suitable vehicle. An antiherpetic concentration generally will be in the range of from about 0.5% of the active compound on a weight/volume basis to saturation (generally about 2 to 6% depending on the vehicle) in the case of a solution. The active compound may also be mixed with a pharmaceutically-acceptable carrier in the form of a suspension or emulsion.

The compounds, method, and compositions described herein may also be used prophylatically at a site where infection or contamination to herpes virus could occur. In such a situation the site of possible infection is treated with an effective virus inhibiting amount of the active compound as already described above so as to prevent infection or contamination with herpes virus. An example of such an operation would be where the birth canal is treated prior to delivery of a newborn to a mother known or suspected to have a history of herpes genitalis to reduce the risk of neonatal herpes of the newborn.

In practicing the method of the invention, the active ingredient is preferably incorporated in a composition comprising a suitable pharmaceutically-acceptable non-aqueous carrier and an effective virus inhibiting concentration of the pyridinyl ketones. To insure stability of the active compounds it is essential that water be excluded from the final composition. Pharmaceutically-acceptable non-aqueous carriers include for example, propylene glycol dipelargonate, isopropyl palmitate, propoxylated stearyl alcohol, and mixtures such as propylene glycol dicaproate (65%) and propylene glycol dicaprylate (35%). Excipients well known to those skilled in the art may be added to the composition to improve the properties and make the composition more cosmetically acceptable.

The following Examples will serve to further clarify the invention, but should not be regarded as a limitation thereon.

EXAMPLE 1

Preparation of 3-(1-piperidinyl)-2-(1-piperidinyl)methyl-1-(3-pyridinyl)-1-propanone In 200 ml of ethanol 34.1 grams (0.4 mole) of piperidine was dissolved. While maintaining the mixture at 5° to 10° C., 32.4 grams (0.4 mole) of 37% formaldehyde solution was slowly added. The reaction mixture was allowed to warm to 20° C. and 24.2 grams (0.2 mole) of 3-acetylpyridine was added. The reaction mixture was stirred at ambient temperature for about one hour, after which it was heated to boiling and maintained at reflux for about four and one half hours. The resulting reaction mixture was poured into about 1 Kg of ice water, and the precipitate collected by filtration. The crude product was dissolved in methylene chloride, dried over magnesium sulfate, and the title compound recovered. The melting point was found to be 80°-82° C.

Elemental analysis showed carbon 72.35%, hydrogen 9.06%, and nitrogen 13.27% as compared to calculated values of carbon 72.34%, hydrogen 9.27%, and nitrogen 13.32%.

Using essentially the same procedure other pyridinyl ketones and their corresponding salts were prepared. These compounds were as follows:

3-(4-methyl-piperidinyl)-2-((4-methyl-1-piperidinyl)-methyl)-1-(3-pyridinyl)-1-propanone dihydrochloride, m.p. 180°-181° C.

3-(3-methyl-1-piperidinyl)-2-((3-methyl-1-piperidinyl)methyl)-1-(3-pyridinyl)-1-propanone dihydrochloride, m.p. 129°-130° C.

3-(3-methyl-1-piperidinyl)-2-((3-methyl-1-piperidinyl)methyl-1-(3-pyridinyl)-1-propanone, m.p. 93°-95° C.

3-(4-methyl-1-piperidinyl)-2-((4-methyl-1-piperidinyl)methyl-1-(3-pyridinyl)-1-propanone, m.p. 83°-85° C.

3-(1-piperidinyl)-2-(1-piperidinylmethyl)-1-(3-pyridinyl)-1-propanone dihydrochloride, monohydrate, softening point 150° C.

All of the compounds disclosed above are satisfactory for use in the method encompassed by the present invention.

EXAMPLE 2

Albino male and female guinea pigs weighing between 300 and 400 grams were inoculated with the Stohr strain of herpes hominis (Type I) applied to the external genitalia/perianal region (perineum) using a spring loaded vaccination instrument. The vaccination instrument was triggered five times at two separate locations on the perineum producing inoculation sites to a depth of 0.75 mm. The inoculation sites were air dried and the guinea pigs returned to individual cages.

A formulation containing 2% w/v 3-(1-piperidinyl)-2-(1-piperidinyl)methyl)-1-(3-pyridinyl)-1-propanone in 98% propylene glycol dipelargonate was applied topically beginning two hours after inoculation with the virus and was repeated at two hour intervals between 8:00 AM and 4:00 PM for three days. The perineum of each guinea pig was examined daily beginning on day four following inoculation with the virus. Viral lesions were counted for each animal and classified as to stage of development. Mean lesion scores were compared by analysis of variance. Modified Wilcoxin or Dunnett's Test were used to compare differences between the lesion scores of the treated group and a group of untreated control animals.

Lesion scores of animals treated with the active compound were significantly lower than those of the untreated control animals ($p < 0.05$).

The compounds 3-(3-methyl-1-piperidinyl)-2-((3-methyl-1-piperidinyl)methyl)-1-(3-pyridinyl)-1-propanone and 3-(4-methyl-1-piperidinyl)-2-((4-methyl-1-piperidinyl)methyl)-1-(3-pyridinyl)-1-propanone were tested in a isopropyl palmitate carrier at concentrations of 2%, 1% and 0.5% using the general procedure described above. Lesion scores of all treated animals at each of the concentration levels was significantly lower than those of control animals ($p < 0.05$).

The salt 3-(1-piperidinyl)-2-(1-piperidinylmethyl)-1-(3-pyridinyl)-1-propanone dihydrochloride, monohydate was tested in a similar manner to that described above and was confirmed as effective in the control of herpes infections.

I claim:

1. A method for treating herpes virus infections in a mammal infected with herpes virus which comprises administering to said mammal an effective virus inhibiting amount of a pyridinyl ketone or a pharmaceutically-acceptable salt thereof, said pyridinyl ketone corresponding to the formula

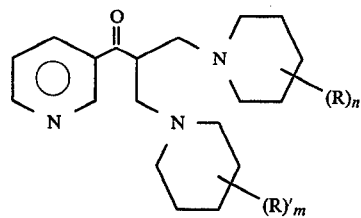

wherein R and R' independently represent a lower alkyl having from 1 to about 3 carbon atoms; n and m independently represent the integer 0 or 1.

2. The method of claim 1 wherein the compound is 3-(1-piperidinyl)-2-(1-piperidinyl)methyl)-1-(3-pyridinyl)-1-propanone or a pharmaceutically-acceptable salt thereof.

3. The method of claim 1 wherein the compound is 3-(3-methyl-1-piperidinyl)-2-((3-methyl-1-piperidinyl)-methyl-1-(3-pyridinyl)-1-propanone or a pharmaceutically-acceptable salt thereof.

4. The method of claim 1 wherein the compound is 3-(4-methyl-1-piperidinyl)-2-((4-methyl-1-piperidinyl)-methyl)-1-(3-pyridinyl)-1-propanone or a pharmaceutically-acceptable salt thereof.

5. The method of claim 1 wherein the compound is applied topically to a mammal infected with herpes virus.

* * * * *